US005837696A

United States Patent [19]
Golub et al.

[11] Patent Number: 5,837,696
[45] Date of Patent: Nov. 17, 1998

[54] METHOD OF INHIBITING CANCER GROWTH

[75] Inventors: Lorne M. Golub, Smithtown; Thomas F. McNamara, Port Jefferson; Nungavaram S. Ramamurthy, Smithtown; Hsi-Ming Lee, Setauket; Sanford Simon, Stony Brook, all of N.Y.; Balakrishna L. Lokeshwar, Miami, Fla.; Marie G. Selzer, Fort Lauderdale, Fla.; Norman L. Block, Miami, Fla.

[73] Assignees: The Research Foundation of State University of New York, Albany, N.Y.; University of Miami, Miami, Fla.

[21] Appl. No.: 783,655

[22] Filed: Jan. 15, 1997

[51] Int. Cl.$^6$ .............................. A01N 37/18; A61K 31/65
[52] U.S. Cl. ........................... 514/152; 514/153; 514/154
[58] Field of Search ................................... 514/152, 154, 514/153

[56] References Cited

U.S. PATENT DOCUMENTS

| 5,308,839 | 5/1994 | Golub et al. | 514/152 |
| 5,321,017 | 6/1994 | Golub et al. | 514/152 |
| 5,563,130 | 10/1996 | Backer | 514/152 |
| 5,567,693 | 10/1996 | Backer et al. | 514/154 |
| 5,574,026 | 11/1996 | Backer et al. | 514/152 |
| 5,668,122 | 9/1997 | Fife et al. | 514/152 |

FOREIGN PATENT DOCUMENTS 12717   8/1992   WIPO .

OTHER PUBLICATIONS

Bassett P, Okada A, Chenard M–P, Kannan R, Stoll I, Anglard P, Bellocq J–P, Rio M–C, "Matrix Metalloproteinases as Stromal Effectors of Human Carcinoma Progression: Therapeutic Implications", *Matrix Biology* 15:535–541 (1997).
Golub LM, Ramamurthy NS, Leungt M, McNamara TF, "Low–Dose Doxycycline Thrapy: Effect on Gingival and Crevicular Fluid Collagenase Activity in Humans", *J. Periodont Res* 25:321–330 (1990).
Golub LM, Lee HM, Lehrer G, Nemiroff A, McNamara TF, Kaplan R, Ramamurthy NS, "Minocycline Reduces Gingival Collagenolytic Activity During Diagetes", *Journal of Periodontal Research* 18:516–526 (1983).
Hatsu M, Sasaki T, Watabe H–O, Miyadoh S, Nagasawa M, Shomura T, Sezaki M, Inouye S, Kondo S, "A New Tetracycline Antibiotic with Antitumor Activity", *The Journal of Antibiotics* 45(3):320–324 (1992).
Hatsu M, Sasaki T, Gomi S, Kodama Y, Sezaki M, Inouye S, Kondo S, "A New Tetracycline Antibiotic with Antitumor Activity", *The Journal of Antibiotics* 45(3):325–330 (1992).

Johnson RK, Goldin A, "The Clinical Impact of Screening and Other Experimental Tumor Studies", *Cancer Treatment Reviews* 2:1–31 (1975).
Okada A, Bellocq J–P, Rouyer N, Chenard M–P, Rio M–C, Chambon P, Basset P, "Membrane–Type Matrix Metalloproteinase (MT–MMP) Gene is Expressed in Stromal Cells of Human Colon, Breast, and Head and Neck Carcinoma", *Proc. Natl. Acad. Sci. USA* 92:2730–2734 (1995).
Okada A, Tomasetto C, Lutz Y, Bellocq J–P, Rio M–C, Basset P, "Expression of Matrix Metalloproteinases During Rat Skin Wound Healing: Evidence that Membrane Type–1 Matrix Metalloproteinase is a Stromal Activator of Pro–Gelatinase A", *The Journal of Cell Biology* 137(1):67–77 (1997).
Sotomayor EA, Teicher BA, Schwartz GN, Holden SA, Menon K, Herman TS, Frei III E, Minocycline in Combination with Chemotherapy or Radiation Therapy in Vitro and in Vivo, *Cancer Chemother Pharmacol* 30:377–384 (1992).
Uitto V–J, Firth JD, Nip L, Golub LM "Doxycycline and Chemically Modified Tetracyclines Inhibit Gelatinase A (MMP–2) Gene Expression in Human Skin Keratinocytes", *Annals of the New York Academy of Sciences* 732:140–151 (1994).
Zeng ZS, Huang Y, Cohen AM, Guillem JG, "Prediction of Colorectal Cancer Relapse and Survival via Tissue RNA Levels of Matrix Metalloproteinase–9", *Journal of Clinical Oncology* 14(12):3133–3140 (1996).
Zucker S. Lysik RM, Ramamurthy NS, Golub LM, Wieman JM, Wilkie DP, "Diversity of Melanoma Plasma Membrane Proteinases: Inhibition of Collagenolytic and Cytolytic Activities by Minocycline", *JNCI* 75(3):517–525 (1985).
Zucker S, Turpeenniemi–Hujanen, T, Ramamurthy N, Wieman J, Lysik R, Gorevic P, Liotta LA, Simon SR, Golub LB, "Purification and Characterization of a Connective–Tissue–Degrading Metalloproteinase from the Cytosol of Metastatic Melanoma Cells", *Biochem. J* 245:429–437 (1987).
Zucker S, Weiman J, Lysik RM, Imhof B, Nagase H, Ramamurthy N, Liotta LA, Golub LM, "Gelatin–Degrading Type IV Collagenase Isolated from Human Small Cell Lung Cancer", *Invasion Metastasis* 9:167–181 (1989).
Johnson et al, Cancer Treatment Reviews vol. 2 p. 1, 1975.

*Primary Examiner*—Sheela Huff
*Attorney, Agent, or Firm*—Hoffmann & Baron, LLP

[57] ABSTRACT

The invention is a method of inhibiting cancer growth, including cellular proliferation, invasiveness, or metastasis in mammals. The method employs 6-demethyl-6-deoxy-4-dedimethylaminotetracycline (CMT-3) and other functionally related chemically modified, preferably non-antibacterial, tetracycline compounds to inhibit cancer growth. The method is particularly effective to inhibit the establishment, growth, and metastasis of solid tumors, such as tumors derived from colon cancer cells, breast cancer cells, melanoma cells, prostatic carcinoma cells, or lung cancer cells.

13 Claims, 8 Drawing Sheets

FIG-1B CYTOTOXICITY OF CMTS ON THE DUNNING TUMOR CELLS

FIG-2A  INHIBITION OF INVASIVITY BY CMTS

FIG-2B  INHIBITION OF INVASIVITY BY CMTS

FIG-3B GROWTH AND METASTASIS OF DUNNING TUMOR IN VIVO

FIG-4A  TUMOR INCIDENCE

FIG-4B  LUNG METASTASIS BY DUNNING MAT LyLu CELLS

METHOD OF INHIBITING CANCER GROWTH

This invention was made with Government support under Grant No. R37 DE-03987 awarded by the National Institutes of Health through the National Institute of Dental Research and Grant No. R29-CA61038 awarded by the National Institutes of Health. The Government has certain rights in the invention.

BACKGROUND OF THE INVENTION

The invention relates to methods of reducing cancer cell proliferation in biological systems. More specifically, the invention relates to the inhibition of solid tumor invasiveness and metastasis in mammals.

Cancer, in all of its myriad manifestations, remains a devastating plague upon mankind. While progress in preventing and treating cancer has been made, including particular success against Hodgkin's lymphoma and certain other forms, many types of cancer remain substantially impervious to prevailing treatment protocols. Typically, cancer is treated by chemotherapy, in which highly toxic chemicals are given to the patient, or by radiotherapy, in which toxic doses of radiation are directed at the patient. While commonly effective to kill huge numbers of cancer cells, these "cytotoxic" treatments also kill extraordinary numbers of healthy cells, causing the patient to experience acute debilitating symptoms including nausea, diarrhea, hypersensitivity to light, hair loss, etc. The side effects of these cytotoxic compounds limits the frequency and dosage at which they can be administered. Such disabling side effects can be mitigated to some degree by using compounds which selectively target cycling cells, i.e., interfering with DNA replication or other growth processes in cells which are actively reproducing. Since cancer cells are characterized by their extraordinary ability to proliferate, such protocols preferentially kill a larger proportion of cancer cells in comparison to healthy cells, but cytotoxicity and ancillary sickness remains a problem.

Other more recent developments include efforts to develop monoclonal antibodies specific for oncogenes or HLA specificities which identify cancer cells with great precision. However, these procedures are very expensive and extremely procedurally elaborate, yet still fail to produce the desired efficacy. Indeed, such procedures have been reported to be effective in only a small subpopulation of treated patients Tetracycline and a number of its chemical relatives form a particularly successful class of antibiotics. Certain of the tetracycline compounds, including tetracycline itself, as well as sporocycline, etc., are broad spectrum antibiotics, having utility against a wide variety of bacteria. The parent compound, tetracycline, has the following general structure:

The numbering system of the multiple ring nucleus is as follows:

Numerous naturally-occurring tetracyclines, including tetracycline as well as its 5—OH (terramycin) and 7—Cl (aureomycin) derivatives, exhibit antibiotic (antimicrobial) properties. Natural tetracyclines may be modified without losing their antibiotic properties, although certain elements of the structure must be retained to do so. The modifications that may and may not be made to the basic tetracycline structure have been reviewed by Mitscher (1978). According to Mitscher, modification at positions 5–9 of the tetracycline ring system can be made without causing the complete loss of antibiotic properties.

However, changes to the basic structure of the ring system, or replacement of substituents at positions 1–4 or 10–12, generally lead to synthetic tetracyclines with substantially less, or essentially no, antibacterial activity. For example, 4-dedimethylaminotetracycline is commonly considered to be a non-antibacterial tetracycline.

During recent years it has been established that tetracyclines, which are rapidly absorbed and have a prolonged half-life, exert biological effects independent of their antimicrobial activity (Golub et al. 1991, Golub et al. 1992, Uitto et al. 1994). Such effects include inhibition of matrix metalloproteinases (abbreviated "MMPs"), including collagenases (MMP-1; MMP-8), gelatinase (MMP-2; MMP-9), and stromelysin (MMP-3) as well as prevention of pathologic tissue destruction (Golub et al. 1991). Recent studies have suggested that certain tetracyclines and inhibitors of metalloproteinases can inhibit tumor progression (DeClerck et al. 1994) and angiogenesis (Maragoudakis et al. 1994). Zucker et al. (1985) showed that minocycline can inhibit melanoma cell activity.

However, the use of tetracycline antibiotics, while generally effective for treating infection, can lead to undesirable side effects. For example, the long term administration of antibiotic tetracyclines can reduce or eliminate healthy flora, such as intestinal flora, and can lead to the production of antibiotic resistant organisms or the overgrowth of yeast and fungi. Accordingly, chemically-modified tetracyclines, in which the antimicrobial activity is attenuated or deleted, can be preferred for use in applications in which anti-collagenolytic activity is indicated.

In view of the above considerations, it is clear that there is a need to supplement existing methods of inhibiting cancer cell invasiveness and metastasis. Current approaches rely on highly cytotoxic compounds which cause ancillary debilitating sickness in patients, or use methodology which is expensive, procedurally difficult, and irreproducible.

Accordingly, it is one of the purposes of this invention to overcome the above limitations in cancer treatment, by providing a compound and method for inhibiting the growth processes characteristic of cancer cells, including inhibiting invasiveness and metastasis, as well as inducing regression of primary tumors. In particular, it is desirable to identify new anticancer compounds and methods which inhibit cancer growth specifically and with relatively high activity, i.e., being active at doses which are substantially free of harmful side effects.

SUMMARY OF THE INVENTION

It has now been discovered that these and other objectives can be achieved by the present invention, which provides a method for inhibiting the growth or development of cancer in a mammal by providing a chemically modified tetracycline to the mammal in an amount which is effective to achieve the specified result.

Specifically, the invention is a method of inhibiting cancer growth in a mammal, comprising administering to the mammal a cancer-inhibitory amount of a tetracycline compound selected from the group consisting of: 4-dedimethylaminotetracycline (CMT-1), 6-demethyl-6-deoxy-4-dedimethylaminotetracycline (CMT-3), 4-dedimethylamino-7-chlorotetracycline (CMT-4), and 6-α-deoxy-5-hydroxy-4-dedimethylaminotetracycline (CMT-8). A particularly preferred tetracycline compound is 6-demethyl-6-deoxy-4-dedimethylaminotetracycline (CMT-3)

The method can be used to inhibit growth of cancers such as carcinomas, in particularly adenocarcinomas. The invention is effective to reduce the growth of adenocarcinomas of the prostate, breast, ovary, testes, or colon as well as melanomas.

The method of the invention can comprise inhibiting cellular proliferation of said cancer, inhibiting invasiveness of said cancer, or inhibiting metastasis of said cancer.

Preferably, the tetracycline compound is administered in an amount sufficient to specifically inhibit expression of a matrix metalloproteinase by cells of said cancer. The method can be used to inhibit gelatinase expression by the cancer cells, especially the expression of gelatinase A or gelatinase B.

The method of the invention can further comprise treating the mammal with an adjunct antineoplastic modality, such as chemotherapy, surgery, or radiotherapy.

In another embodiment, the invention is a method of inhibiting cancer growth in a mammal, comprising topically administering to said mammal a cancer-inhibitory amount of a tetracycline compound selected from the group consisting of: tetracyclinonitrile (CMT-2) and 4-hydroxy-4-dedimethylaminotetracycline (CMT-6).

By means of the invention, a method of inhibiting cancer growth is provided which further avoids or mitigates side effects commonly associated with antineoplastic chemotherapeutic regimens. These and other advantages of the present invention will be appreciated from the detailed description and examples which are set forth herein. The detailed description and examples enhance the understanding of the invention, but are not intended to limit the scope of the invention.

BRIEF DESCRIPTION OF THE DRAWINGS

Preferred embodiments of the invention have been chosen for purposes of illustration and description, but are not intended in any way to restrict the scope of the invention. The preferred embodiments of certain aspects of the invention are shown in the accompanying drawing, wherein:

FIGS. 1A and 1B. FIG. 1A is a graph illustrating the dose dependence of CMT-3 cytotoxicity in Dunning tumor cells at 24 hr exposure in vitro; while

FIGS. 2A and 2B.

FIGS. 3A and 3B.

FIGS. 4A and 4B.

DETAILED DESCRIPTION OF THE PREFERRED EMBODIMENTS

The present invention is directed to a method for inhibiting cancer cell growth, including processes of cellular proliferation, invasiveness, and metastasis in biological systems. The method includes the use of a tetracycline compound as an inhibitor of cancer cell growth. Preferably, the method is employed to inhibit or reduce cancer cell growth, invasiveness, metastasis, or tumor incidence in living animals, such as mammals. The method is also readily adaptable for use in assay systems, e.g., assaying cancer cell growth and properties thereof.

The compounds useful according to the invention possess a desirable but unusual combination of properties, including activity, solubility, and reduction of side effects. These compounds have been found to inhibit cancer growth, including proliferation, invasiveness, and metastasis. Applicants surmise that these compounds exhibit beneficial physicochemical properties which render them particularly desirable for the treatment of cancer. In particular, these compound exhibit their cancer-inhibitory properties at concentrations which are substantially free of side effects. For example, the useful concentrations of the compounds do not present any significant antimicrobial activity. These tetracycline compounds are useful for extended treatment protocols, where other compounds would exhibit undesirable side-effects. In addition, it is believed that the properties of hydrophilicity and hydrophobicity are well balanced in these compounds, enhancing their utility both in vitro and especially in vivo, while other compounds lacking such balance are of substantially less utility. Specifically, the compounds have an appropriate degree of solubility in aqueous media to permit absorption and bioavailability in the body, while also having a degree of solubility in lipids to permit traversal of the cell membrane to a putative site of action. Thus, it is believed that the compounds are maximally effective if they can be delivered to the site of the tumor and are able to enter the tumor cells.

In the treatment of certain localized cancers, the degree of hydrophilicity of the non-antimicrobial tetracycline compound can be of lesser importance. Such compounds as tetracyclinonitrile (CMT-2) and 4-hydroxy-4-dedimethylaminotetracycline (CMT-6), which have low solubility in aqueous systems, can be used in direct or topical treatment of skin cancers, e.g., melanoma or basal cell carcinoma, or by implantation into the brain to topically treat brain cancer.

The invention has been developed based on the unexpected observation by Applicants that certain tetracycline compounds, chemically modified to eliminate substantially all antimicrobial activity, are effective to inhibit the proliferation, invasiveness, or metastasis of cancer cells in vitro, as well as in vivo. Of these, one especially preferred CMT, i.e., 6-demethyl-6-deoxy-4-dedimethylaminotetracycline (also referred to as "CMT-3"), appears to possess an excellent balance of properties, in that it is shown to possess unusually strong activity in inhibiting the cancer growth, including proliferation, invasiveness, or metastasis of cancer cells. Another advantage of CMT-3 is that it has an unexpectedly long serum half-life (approximately 30 days). Therefore, CMT-3 may only require episodic administration, e.g., once per week.

Applicants were surprised to find that CMTs can act by a fundamentally unknown mechanism in the context of cancer. Applicants have discovered that the chemically modified tetracyclines decrease the level of expression of ("down-regulate") metalloproteinases normally associated with cancer. For example, it has been found that CMT-3 reduces expression of gelatinase A (72 kDa type; MMP-2; type IV collagenase) by human colorectal cancer cells, and inhibits expression of gelatinase B (92 kDa type; MMP-9; type V collagenase) by human breast cancer cells. Applicants are not presently aware of any theoretical basis which might explain this unexpected activity of CMTs at the level of gene expression. Nonetheless, Applicants believe that this observation carries significant therapeutic implications for cancer treatment. Applicants also understand that these CMTs and other chemically and functionally related compounds would be useful for inhibiting the consequences of other diseases characterized by excessive gelatinase expression or activity. Such compounds include, for example, those which lack the dimethylamino group at position 4 of the tetracycline ring structure, e.g., 4-dedimethylaminotetracycline (CMT-1), tetracyclinonitrile (CMT-2), 6-demethyl-6-deoxy-4-dedimethylaminotetracycline (CMT-3), 4-dedimethylamino-7-chlorotetracycline (CMT-4), 4-hydroxy-4-dedimethylaminotetracycline (CMT-6), 4-dedimethylamino-12a-deoxytetracycline (CMT-7), and 6a-deoxy-5-hydroxy-4-dedimethylaminotet (CMT-8), 7-dimethylamino-6-demethyl-6-deoxy-4-dedimethylaminotetracycline (CMT-10), 4-dedimethylamino-5-oxytetracycline, 5a,6-anhydro-4-hydroxy-4-dedimethylaminotetracycline, 4-dedimethylamino- 11-hydroxy-12a-deoxytetracycline, 1 2a-deoxy-4-deoxy-4-dedimethylaminotetracycline, and 12a, 4a-anhydro-4-dedimethylaminotetracycline. Further examples of tetracyclines modified for reduced antimicrobial activity include 6-α-benzylthiomethylenetetracycline, the mono-N-alkylated amide of tetracycline, 6-fluoro-6-demethyltetracycline, or 11α-chlorotetracycline.

The cancers treatable by means of the present invention occur in mammals. Mammals include, for example, humans, as well as pet animals such as dogs and cats, laboratory animals such as rats and mice, and farm animals such as horses and cows.

Tumors or neoplasms include new growths of tissue in which the multiplication of cells is uncontrolled and progressive. Some such growths are benign, but others are termed "malignant," leading to death of the organism. Malignant neoplasms or "cancers" are distinguished from benign growths in that, in addition to exhibiting aggressive cellular proliferation, they invade surrounding tissues and metastasize. Moreover, malignant neoplasms are characterized in that they show a greater loss of differentiation (greater "dedifferentiation"), and of their organization relative to one another and their surrounding tissues. This property is also called "anaplasia."

Neoplasms treatable by the present invention include all solid tumors, i.e., carcinomas and sarcomas. Carcinomas include those malignant neoplasms derived from epithelial cells which tend to infiltrate (invade) the surrounding tissues and give rise to metastases. Adenocarcinomas are carcinomas derived from glandular tissue or in which the tumor cells form recognizable glandular structures. Another broad category or cancers includes sarcomas, which are tumors whose cells are embedded in a fibrillar or homogeneous substance like embryonic connective tissue.

The invention is particularly illustrated herein in reference to treatment of certain types of experimentally defined cancers. In these illustrative treatments, standard state-of-the-art in vitro and in vivo models have been used. These methods can be used to identify agents which can be expected to be efficacious in in vivo treatment regimens. However, it will be understood that the method of the invention is not limited to the treatment of these tumor types, but extends to any solid tumor derived from any organ system. Cancers whose invasiveness or metastasis is associated with MMP expression, especially gelatinase expression, are especially susceptible to being inhibited or even induced to regress by means of the invention.

Thus, the treatable cancers include cancers such as, for example, colon cancer, bladder cancer, breast cancer, melanoma, ovarian carcinoma, prostatic carcinoma, or lung cancer, and a variety of other cancers as well. The invention is especially useful in the inhibition of cancer growth in adenocarcinomas, including, for example, those of the prostate, breast, kidney, ovary, testes, and colon. The invention is further useful against melanomas, which derive from, the melanocytic system in the skin and other organs.

The method involves the providing or administering a tetracycline compound in an amount which is effective for reducing cancer cell growth, i.e., cellular proliferation, invasiveness, or metastasis in a mammal. The inhibition may result from inhibition of MMP activity, down-regulation of MMP expression, some other mechanism, or a combination of mechanisms. For example, Applicants have found that CMT-3 inhibits the expression of MMP-2 and MP-9 in cancer cells in vitro. It is believed that all solid cancer types which express MMPs or which exhibit invasive or metastatic properties can be treated by the method of the invention. In some cases, the development of tumor foci can be substantially prevented from occurring. Therefore, the method can be used as a prophylactic treatment, e.g., by administering the tetracycline compound to a mammal after detection of a gene product or metabolite associated with predisposition to a cancer but before any specific cancerous lesion is detected. The tetracycline compounds useful according to the invention are especially advantageous as they are substantially non-toxic compared to other cancer treatments.

The effect occurs over a wide range of concentrations, including at concentrations which are extraordinarily low. The amount of the tetracycline compound used according to the invention is an amount that is effectively inhibitory of cancer growth. An amount of a tetracycline compound is effectively inhibitory to cancer growth if it significantly reduces cellular proliferation or invasiveness or metastasis. Proliferation refers to the capacity of a tumor to increase its volume through cell division, typically measured as the "doubling rate." The inhibition of cellular proliferation by the present method can actually induce regression or diminution of tumor mass, if the rate of replenishment of the tumor cells through cell division is exceeded by the rate of cell death. Invasiveness refers to the capacity of a tumor to invade other tissues, typically by breaking down the extracellular matrix of those tissues. Metastasis refers to the capacity of a tumor to establish new tumor foci at sites distant from the primary site where the tumor began. Typically, metastasis proceeds by individual cells or groups of cells breaking off from the primary tumor and migrating, e.g., through the blood or lymph, to establish a new tumor focus in another tissue or organ. One locus common in tumor metastasis is in the lung, where the very fine vasculature of the lung tissue can often catch circulating tumor cells, permitting the establishment of a tumor focus therein. Some types of tumors metastasize to specific types of tissues. For example, prostate adenocarcinomas can metastasize to bone with great specificity. The data presented herein provide evidence that the method of the invention is capable of inhibiting cancer growth as defined by any or all of these parameters.

Preferably, the tetracycline compound is provided in an amount which has little or no antimicrobial activity. A tetracycline compound is not effectively antimicrobial if it does not significantly prevent the growth of microbes. Accordingly, the method can beneficially employ a tetracycline compound which has been modified chemically to reduce or eliminate its antimicrobial properties. The use of such chemically-modified tetracyclines is preferred in the present invention since they can be used at higher levels than antimicrobial tetracyclines, while avoiding certain disadvantages, such as the indiscriminate killing of beneficial microbes, and the emergence of resistant microbes, which often accompanies the use of antimicrobial or antibacterial amounts of such compounds.

The tetracycline compounds useful according to the method of the invention appear to exhibit their beneficial effect in a dose-dependent manner. Thus, within broad limits, administration of larger quantities of a tetracycline compound has been observed to inhibit cancer cell growth or invasiveness to a greater degree than does administration of a smaller amount. Moreover, efficacy has been observed at dosages below the level at which toxicity is seen. Accordingly, one of the advantages of the invention is that the debilitating side effects usually attendant upon cytotoxic cancer treatments are avoided.

The maximal dosage for a subject is the highest dosage which does not cause undesirable or intolerable side effects. For example, the tetracycline compound can be administered in an amount of from about 0.1 mg/kg/day to about 30 mg/kg/day, and preferably from about 1 mg/kg/day to about 18 mg/kg/day. For the purpose of the present invention, side effects may include clinically significant antimicrobial or antibacterial activity, as well as toxic effects. For example, a dose in excess of about 50 mg/kg/day would likely produce side effects in most mammals, including humans. In any event, the practitioner is guided by skill and knowledge in the field, and the present invention includes, without limitation, dosages which are effective to achieve the described phenomena.

The compound useful according to the present invention include 4-dedimethylaminotetracycline (CMT-1), 6-demethyl-6-deoxy-4-dedimethylaminotetracycline (CMT-3), 4-dedimethylamino-7-chlorotetracycline (CMT-4), and 6-α-deoxy-5-hydroxy-4-dedimethylaminotetracycline (CMT-8). The most preferred tetracycline compound is 6-demethyl-6-deoxy-4-dedimethylaminotetracycline (CMT-3). Doxycycline is not included within the invention.

The invention can also be practiced by including with the tetracycline compound another anti-cancer chemotherapeutic agent, such as any conventional chemotherapeutic agent. The combination of the tetracycline compound with such other agents can potentiate the chemotherapeutic protocol. Numerous chemotherapeutic protocols will present themselves in the mind of the skilled practitioner as being capable of incorporation into the method of the invention. Any chemotherapeutic agent can be used, including alkylating agents, antimetabolites, hormones and antagonists, radioisotopes, as well as natural products. For example, the non-anti-microbial tetracycline compound can be administered with antibiotics such as doxorubicin and other anthracycline analogs, nitrogen mustards such as cyclophosphamide, pyrimidine analogs such as 5-fluorouracil, cisplatin, hydroxyurea, taxol and its natural and synthetic derivatives, and the like. As another example, in the case of mixed tumors, such as adenocarcinoma of the breast, where the tumors include gonadotropin-dependent and gonadotropin-independent cells, the tetracycline can be administered in conjunction with leuprolide or goserelin (synthetic peptide analogs of LH-RH). Other antineoplastic protocols include the use of a tetracycline compound with another treatment modality, e.g., surgery, radiation, etc., referred to herein as "adjunct antineoplastic modalities." Thus, the method of the invention can be employed with such conventional regimens with the benefit of reducing side effects and enhancing efficacy.

The preferred pharmaceutical composition for use in the method of the invention includes a combination of the tetracycline compound in a suitable pharmaceutical carrier (vehicle) or excipient as understood by practitioners in the art. Enteral administration is a preferred route of delivery of the tetracycline, and compositions including the tetracycline compound with appropriate diluents, carriers, and the like are readily formulated. Liquid or solid (e.g., tablets, gelatin capsules) formulations can be employed. Parenteral use (e.g., intravenous injection) is also contemplated, and formulations using conventional diluents, carriers, etc., such as are known in the art can be employed to deliver the compound. Alternatively, delivery of the tetracycline compound can include topical application. Compositions deemed to be suited for such topical use include as gels, salves, lotions, ointments and the like.

In developing the present invention, several chemically modified tetracyclines (CMTs) were tested for their effect (in comparison to a commercially available antibacterial tetracycline, doxycycline) in inhibiting cancer growth. This testing investigated the effect of these compounds on prostate cancer cell proliferation and invasive potential in vitro, and on tumor growth and lung colonization of an in vivo tumor model, the rat Dunning MAT LyLu. Doxycycline and certain other CMTs inhibited the cell proliferation of human prostate tumor cell lines (PC-3, DU-145, TSU-PR1, and LNCaP), and the Dunning prostate tumor cells ($IC_{50}$=12–40 µg/mL). Doxycycline and CMTs also inhibited invasive potential by 10% to 90%, depending on the compound. CMT-3 (6-deoxy-6-demethyl-4-dedimethylaminotetracycline) was the most potent of the tetracycline analogues, inhibiting invasive potential by 90% at 5 µg/mL. Growth of the Dunning tumor at the primary site (s.c.) was not altered significantly in rats treated with either doxycycline or CMT-3 by oral gavage daily for 21 days following tumor implant. There was a significant decrease, however, in the number of lung metastases: 28.9±15.4 sites/animal in the CMT-3-treated group versus 59.5±13.9 sites/animal in controls (p<0.01). Predosing the rats 7 days prior to tumor implant resulted in a significant delay in tumor growth (46±9.3%, p<0.05) and a reduction in metastasis. In addition, tumor remission (inhibition of tumor incidence) occurred in the groups treated with CMT-3 (40 mg/kg). Treatment with doxycycline, however, did not result in tumor remission. In addition, a 58±8% decrease in the number of lung metastases was observed in the CMT-3- treated group versus a decrease of 33±7.0% in the doxycycline group. No significant drug-induced morbidity was observed in any of the experiments described herein. These results further substantiate the usefulness of CMT-3 for chemotherapeutic treatment to control tumor aggression and prevent metastasis.

The following examples are provided to assist in a further understanding of the invention. The particular materials and conditions employed are intended to be further illustrative of the invention and are not limiting upon the reasonable scope thereof

EXAMPLE 1

Inhibition of Gene Expression in Cancer Cells

Two human cancer-derived cell lines were obtained from the American Type Culture Collection (ATCC) in Rockville, Md. The cell lines included COLO 205, a human colon cancer-derived cell line which expresses MMP-2 or gelatinase A, and E- 10, a human breast cancer-derived cell line which expresses MMP-9 or gelatinase B.

Cells of each cell line were cultured in 75 cm$^2$ T-flasks in RPMI-1640 (Gibco) with 10% heat-inactivated fetal bovine serum (FBS) containing 100 units/mL penicillin and 100 μL/mL streptomycin. The cells were fed every two days, and passaged every week. The cells were grown to 80–90% confluence, and then the FBS-containing medium was replaced with serum-free medium (SFM). CMT-3 (CollaGenex Pharmaceuticals, Inc., Newtown, Pa.) was added in several concentrations to the cells in SFM. Conditioned medium was collected after 24 hr, centrifuged to remove cell debris, and then assayed for MMP gene expression by Western blot using a conventional technique, and scanning the blots with laser densitometer. The data obtained are summarized in Table 1, below.

TABLE 1

Percent Inhibition of MMP Gene Expression in Cancer Cell Lines by CMT-3

| Cancer Cell Line | CMT-3 Concentration | | |
|---|---|---|---|
| | 0 μM | 10 μM | 20 μM |
| COLO 205 (expressing MMP-2) | — | 13.3% | 66.9% |
| E-10 (expressing MMP-9) | — | 45.3% | 60.8% |

These data clearly show dose-dependent activity of CMT-3 in inhibiting expression of two different MMP genes in two different types of cancer cells. It is believed that the inhibition of MMP expression inhibits the ability of these cancer cells to degrade the extracellular matrix of healthy tissues thereby limiting the cancer's ability to invade such healthy tissues. The inhibition of cancer cell proliferation in vitro and cancer metastasis in vivo is demonstrated in several following examples.

EXAMPLES 2–5

In Examples 2–5, below, the following materials and methods were employed:

Reagents: Chemically modified tetracyclines were prepared according to known methods. The synthesis of various CMTs is extensively documented. See, e.g., Mitscher (1978). The following CMTs were investigated: 4-dedimethylaminotetracycline (CMT-1), tetracyclinonitrile (CMT-2), 6-demethyl-6-deoxy-4-dedimethylaminotetracycline (CMT-3), 4-dedimethylamino-7-chlorotetracycline (CMT-4), 4-hydroxy-4-dedimethylaminotetracycline (CMT-6), 4-dedimethylamino-12a-deoxytetracycline (CMT-7), and 6-α-deoxy-5-hydroxy-4-dedimethylaminotetracycline (CMT-8). Highly purified CMT-3 (93–98%) used for animal studies was supplied by CollaGenex, Inc., Newtown, Pa. Doxycycline was purchased from Sigma Chemical Co., St. Louis, Mo. Matrigel, a solubilized preparation of tumor basement membrane was obtained from Collaborative Research, Bedford, Mass. Boyden Chemotaxis assay chambers (Transwells) were obtained from Costar/Corning Corp., Boston, Mass. All other reagents were from Sigma Chemical Co.

Cells and Tumor Lines: Human prostate cancer cell lines, PC-3, DU-145 and LNCaP were obtained from American Type Culture Collection, Rockville, Md. TSU-PR1, a human metastatic prostatic cancer cell line, was obtained from Dr. Christina Rangel, at the University of Tennessee, Memphis, Tenn. Cultures were maintained in complete medium composed of RPMI-1640 with 10% fetal bovine serum and gentamicin (10 μg/mL). The Dunning MAT LyLu tumor line, which metastasizes to lymph node and lungs in Copenhagen rats, was obtained from Dr. John T. Isaacs, Johns Hopkins Oncology Center, Baltimore, Md. MAT LyLu cells were maintained in the complete medium with added 250 nM dexamethasone.

Tumor Generation and Treatment: Dunning MAT LyLu cells were harvested from culture flasks and a 0.5 mL suspension containing from 2×10$^5$ to 2×10$^6$ cells/mL (see results) were implanted on the dorsal flank of adult Copenhagen rats (Harlan Sprague Dawley, Indianapolis, Ind.). The rats weighed 250–300 g, and were 90–100 days old. Tumors were detected by palpating the skin around the site of injection from 3 days after injecting the tumor cells.

Drug Treatment In Vivo: Doxycycline and CMT-3 were dissolved in a 2% aqueous solution of a soluble form of carboxyrnethyl cellulose (Sigma Cat. No. C-5678), and a fresh solution was made up daily. Rats were gavaged daily with 1 mL of the drug solution, or the vehicle (2% carboxymethyl cellulose). Tumor growth was recorded three times a week, and rats were weighed weekly. The effect of various treatments on tumor growth was monitored over time using calipers, and the volume approximated to an ellipsoid (i.e., volume=length×width×height×0.5236). Tumor growth rate was determined by regression analysis of tumor volume versus time, for each of tumor bearing rats. Mean tumor growth rate (time to reach a fixed volume) for each treatment group was then used to evaluate statistical significance of treatment efficacy using the INSTAT statistical program (Ravitz Software, San Diego, Calif.). Rats were euthanized once the tumor volume reached ≧10 cm$^3$. At that time animals were necropsied, tumors and lungs were removed and fixed in Bouin's fixative. Macroscopic tumor foci on the lungs were counted under a dissecting microscope.

EXAMPLE 2

Effect of CMTs on Prostate Cancer Cell Proliferation In Vitro

To determine the cytotoxicity of CMTs on prostate tumor cell lines, TSU-PR1 cells were exposed to various CMTs or to doxycycline for 24 hr or 48 hr in a serum-free medium. Cell viability (percent of live cells) was estimated by counting the cells following trypan blue staining. Cellular viability was also estimated by the tetrazolium dye reduction assay (MTT assay). Due to the aggressive proliferative capacity of cancer cells, it is assumed that viable cells are actively proliferating. Therefore, the measurement of viability was used as an estimate of proliferation. Results are Mean±SEM from three separate experiments.

It was found that doxycycline and several CMTs reduced cellular viability and, hence, inhibited cell proliferation, in vitro. Inhibition of cell proliferation was proportional to concentration of the drugs and duration of exposure, but varied considerably from compound to compound. In particular, CMT-2 and CMT-3 were significantly more cytotoxic than doxycycline. For the two human prostate cancer cell lines DU-145 and TSU-PR1, the 50% inhibition dose ($IC_{50}$) for various CMTs ranged from 12 µg/mL (CMT-3, 48 hr exposure) to 120 µg/mL (CMT-6). The $IC_{50}$ for CMT-2 was 15 µg/mL. CMT-5 was not inhibitory. Similar results were obtained for other prostatic carcinoma cell lines (data not shown). It is believed that the inhibitory activity of doxycycline and CMTs was due to both cytotoxic and cytostatic effects. For example, DU-145 cells treated for 24 hr with CMT-3 at 15 µg/mL (an $IC_{50}$ dose) showed 12±3.5% dead cells by trypan blue staining, significantly lower than the expected 50%.

Figure 1A:
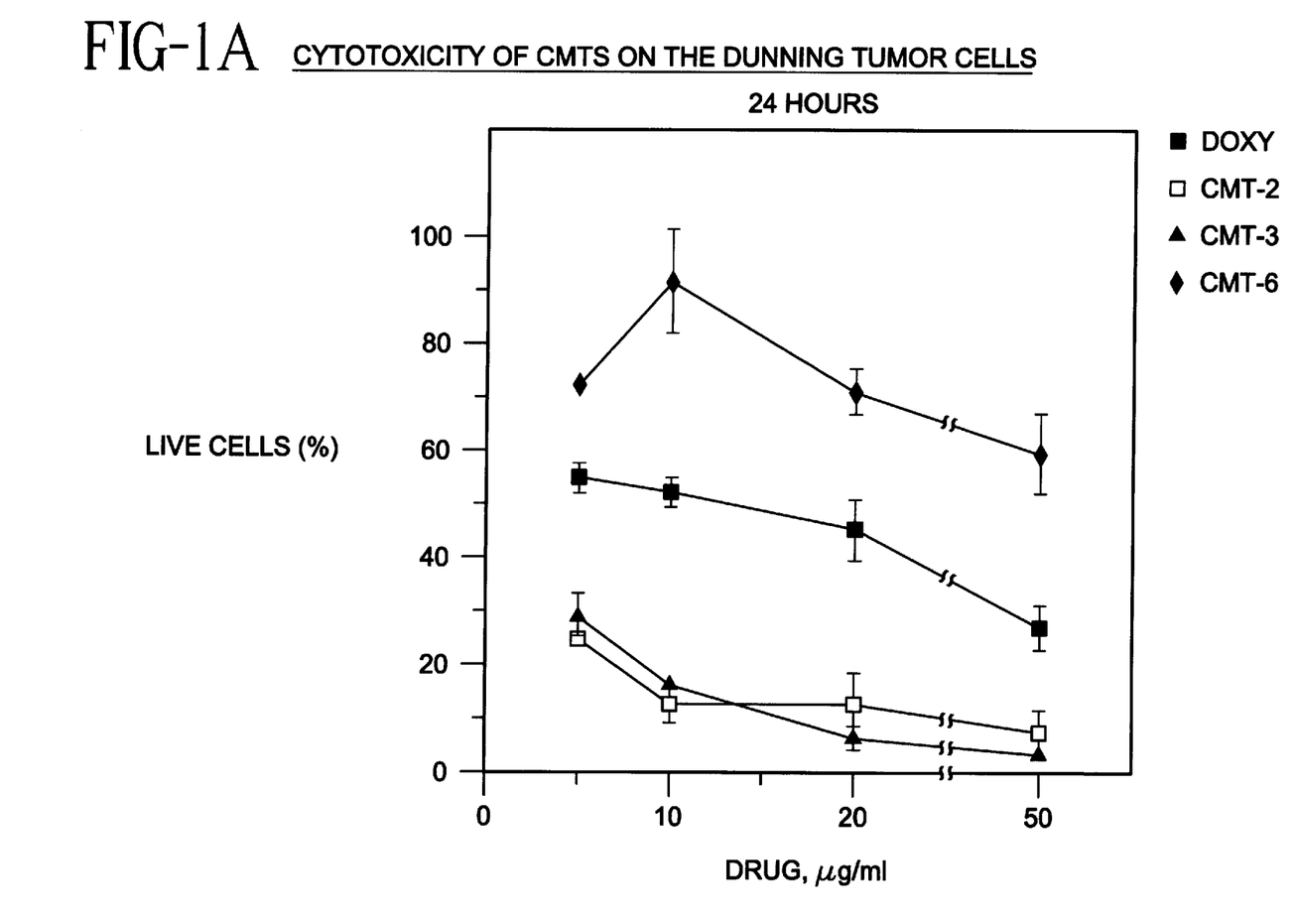
Figure 1B:
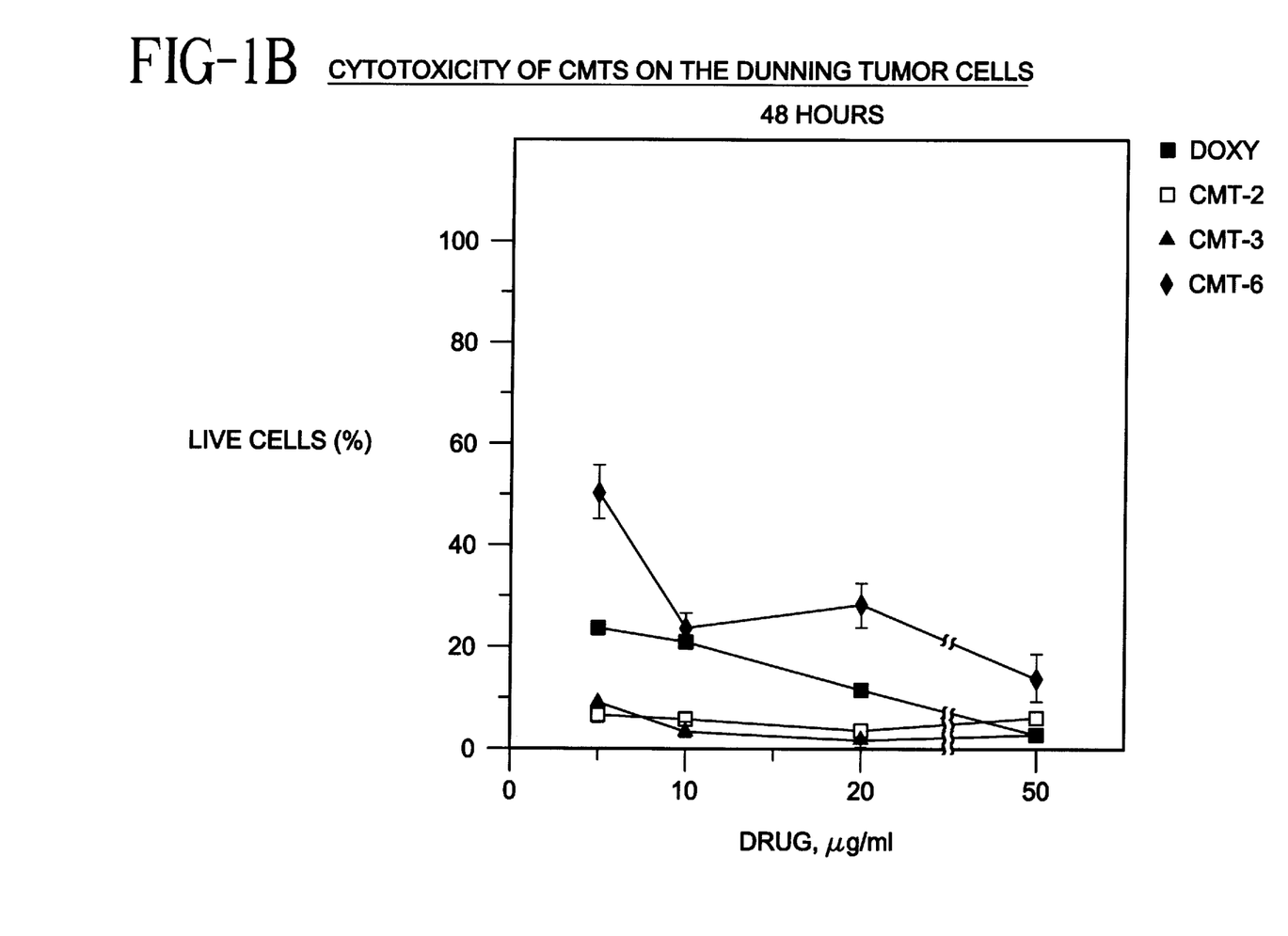
FIG. 1B is a graph illustrating the dose dependence of CMT-3 cytotoxicity in Dunning MAT LyLu tumor cells at 48 hr exposure.

Similar results were obtained when doxycycline and several CMTs (CMT-2, CMT-3, and CMT-6) were tested on the Dunning MAT LyLu cells in vitro. The Dunning MAT LyLu cells were exposed to the drugs for 24 hr or 48 hr before estimating the cellular viability. Cell viability was estimated by trypan blue staining following exposure to the drugs. The results of these studies are summarized in FIG. 1A (24 hours) and FIG. 1B (48 hr). Data are presented as Mean±SEM from three separate experiments. Again, CMT-3 and CMT-2 were the most effective inhibitors of cell proliferation.

EXAMPLE 3

Effect of CMTs on Invasive/Metastatic Potential of Prostate Cancer Cells

Treating prostate cancer cells with certain CMTs significantly inhibited the cells' ability to invade an artificial construct of tumor basement membrane. In this method, $4 \times 10^5$ tumor cells were plated on the top chamber of the Boyden chemotactic assay chamber (Costar Transwell plates). The bottom side of the chamber was a 12 µm-pore polycarbonate filter layered with 0.5 mm thick coat of Matrigel (a solubilized preparation of tumor basement membrane). The bottom well contained a chemoattractant, a conditioned medium from a stromal fibroblast culture. Cancer cells ($4 \times 10^5$) were plated in the top wells of the plates. Doxycycline or CMTs were diluted in a serum-free medium to 5 µg/mL, and were added to both top and bottom chambers. The control wells contained only 0.1% dimethyl sulfoxide (a diluent). Cells at the top chamber and those which invaded the Matrigel coated filter and accumulated at the bottom were quantitated (invasion index) using the MTT assay after 48 hr. Invasiveness was calculated on the basis of an "invasion index," defined as the ratio between the absorbance of the reduced MTT (formazan) of the bottom wells and that of the bottom plus top (i.e., total absorbance). Results presented are from three independent experiments.

Figure 2A:
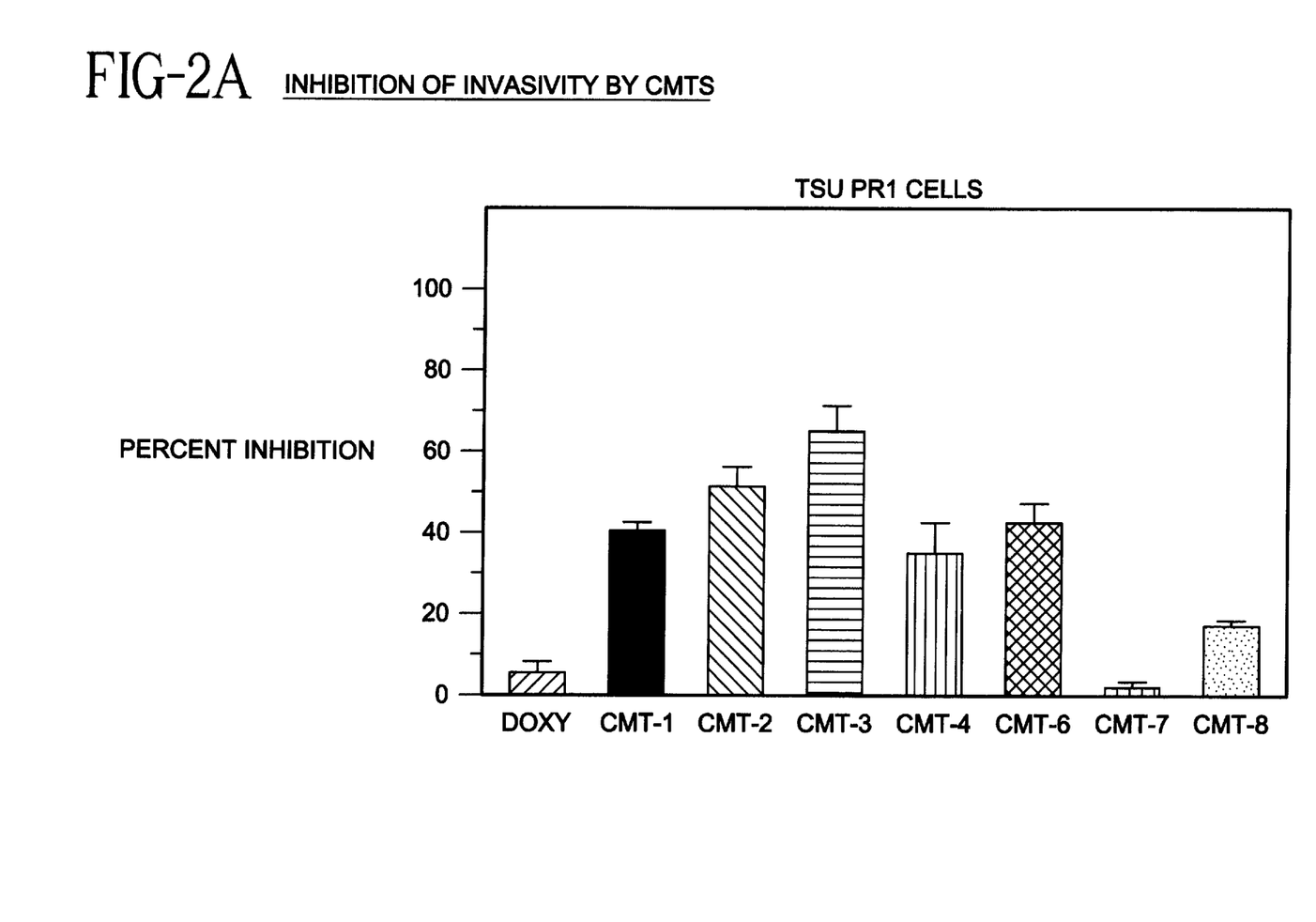
FIG. 2A is a histogram providing a comparative illustration of the capacity of CMT compounds to inhibit invasiveness of TSU-PR1 tumor cells in vitro.

The effect of CMT-3 and other tetracycline compounds on the invasive potential of TSU-PR1 and the Dunning MAT LyLu cells was evaluated using this Matrigel assay. As shown in FIG. 2A, the ability of these compounds to inhibit invasive activity varied significantly. CMT-3 was the most potent, and CMT-7 the least potent, inhibitor of invasive/metastatic potential of TSU-PR1 cells. The CMTs were surprisingly effective compared to a common tetracycline, doxycycline, which caused only a modest (8±1.8%) inhibition of Matrigel invasion of TSU-PR1 cells.

Figure 2B:
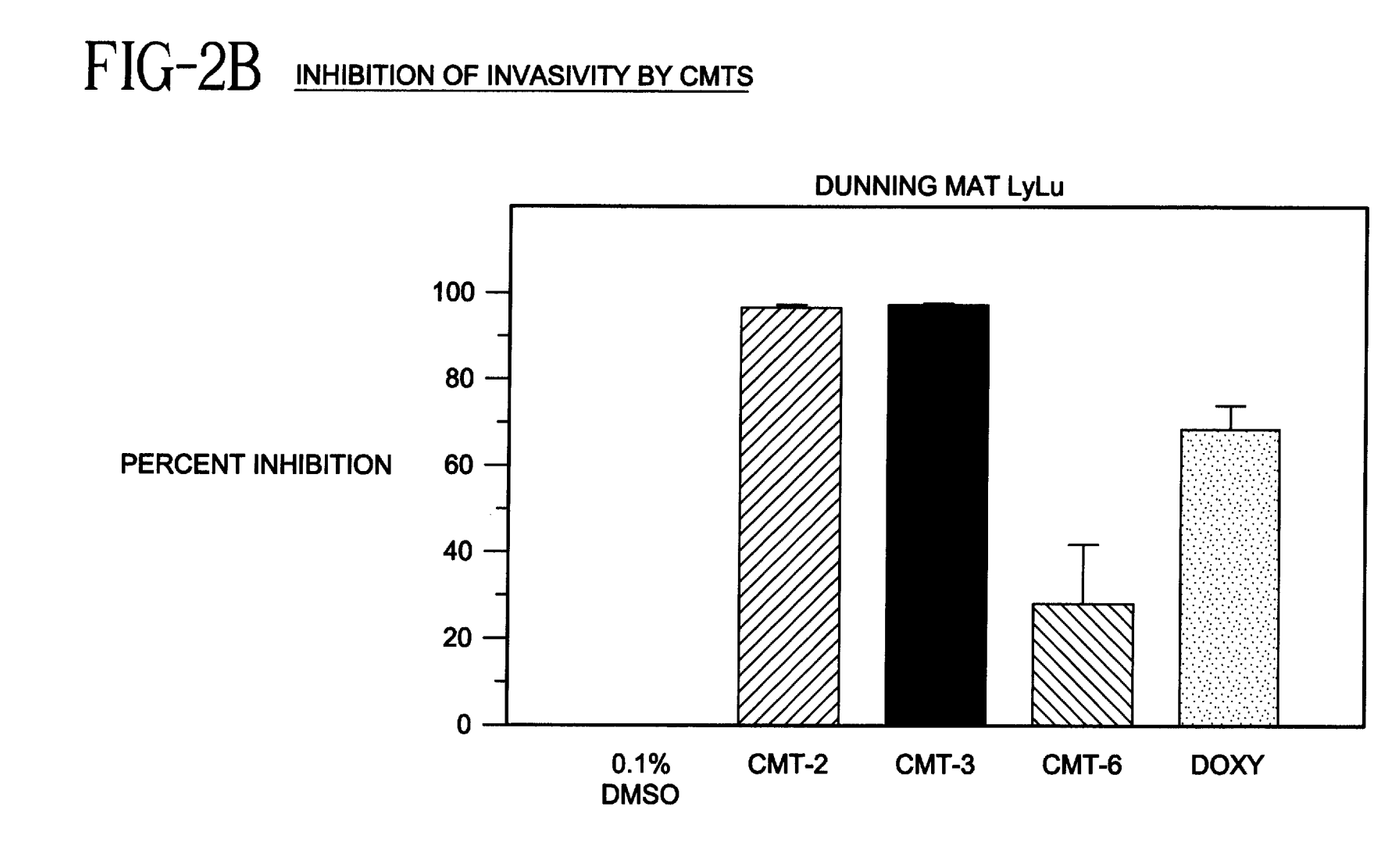
FIG. 2B is a histogram providing a comparative illustration of the capacity of CMT compounds to inhibit invasiveness of Dunning MAT LyLu tumor cells in vitro.

In the Dunning cells, both CMT-2 and CMT-3 equally inhibited Matrigel invasion. See FIG. 2B. Moreover, doxycycline also significantly (68±4.2%) inhibited invasive/metastatic potential of the Dunning MAT LyLu cells over a 48 hr period. Continuous presence of the drugs was needed to achieve significant inhibition of invasive potential. Pretreatment up to 48, hours, but with deletion of the drugs in the invasion chamber, had only moderate effect on the invasive potential.

The invasion index of control (0.1% DMSO) wells was 22±8.3% for TSU-PR1 cells and 17±4.2 for MAT LyLu cells for the 48 hr invasion assay.

EXAMPLE 4

Effect of CMT-3 on Dunning Tumor Growth and Lung Metastasis

Figure 3A:
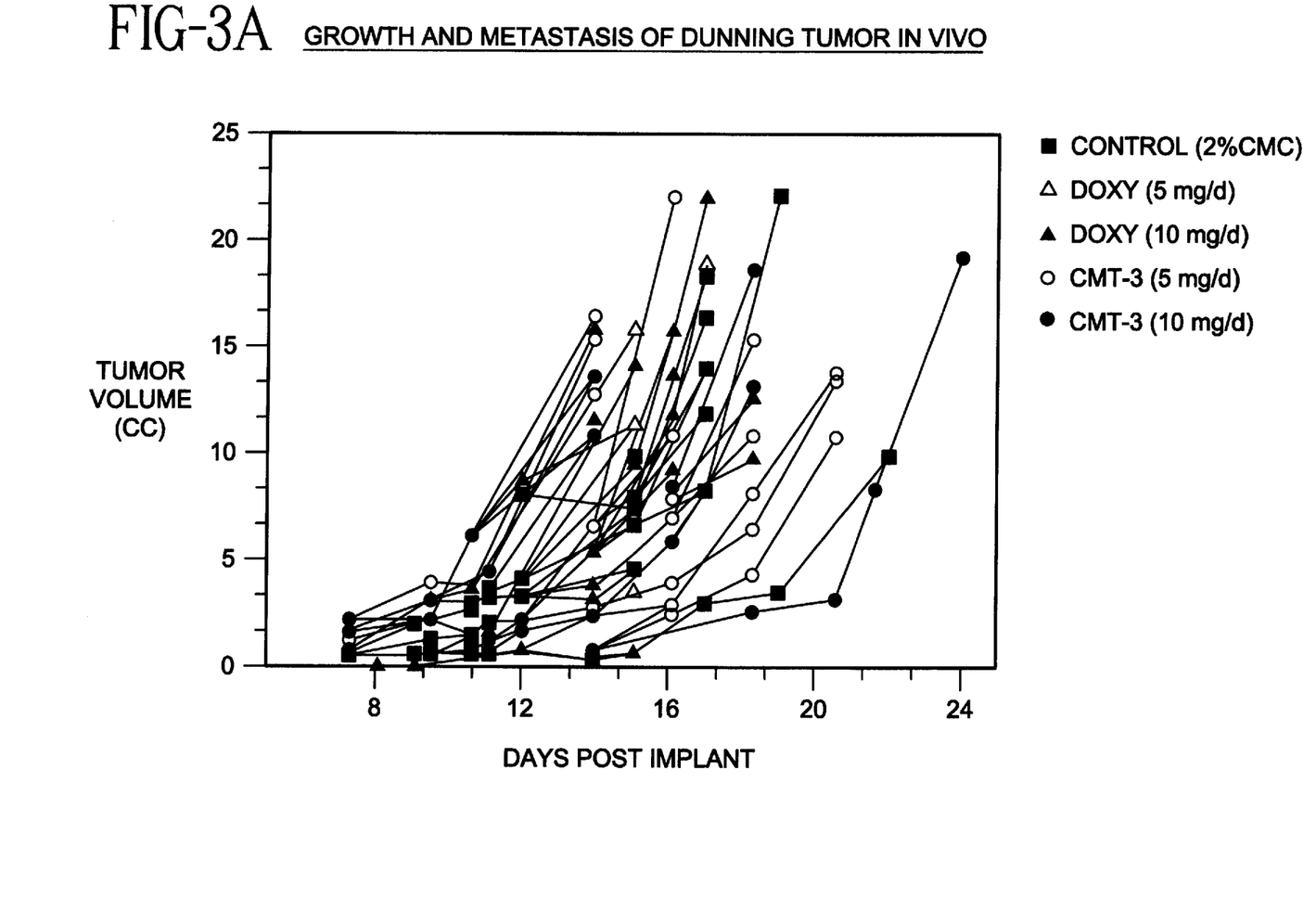
FIG. 3A is a graph illustrating the relationship between tumor volume and time following implantation of tumor cells into test animals.

Tumor cell injection and the drug treatment were started simultaneously. Tumor growth was initiated by sub cutis injection of $1 \times 10^6$ tumor cells. Drug dosing began the same day. On day six, tumors were palpable ($\geq 0.1$ $cm^3$) in more than 50% of injected animals. Tumor growth rate, as determined by the period to reach a volume of 3 $cm^3$, did not vary significantly between rats treated with doxycycline (20 mg/kg, 40 mg/kg) or CMT-3 and the vehicle alone (2% solution of carboxymethyl cellulose). FIG. 3A shows the growth profile of tumors in each rat. As shown in FIG. 3A, growth rate of primary tumor (at the site of injection) was not significantly different between drug treated and control groups. For example, the time period from injection of cells to a growth of 3 $cm^3$ tumor was 13.57±2.12 days in the control group and 14.0±1.9 days in the CMT-3-treated group. All of the tumors, from the control group as well from the drug-treated group developed highly necrotic centers as the tumors grew to 10 $cm^3$ or larger.

Figure 3B:
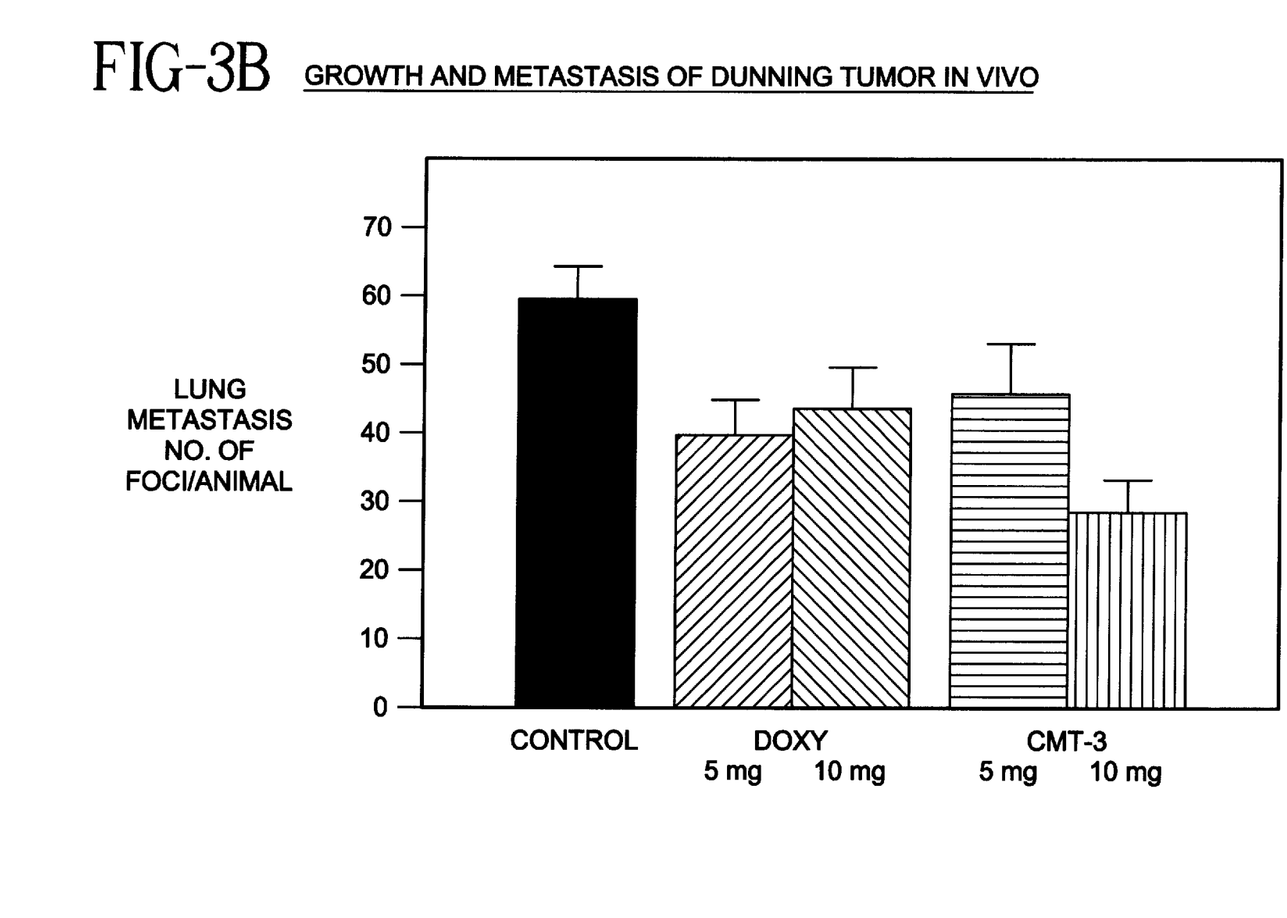
FIG. 3B is a histogram illustrating the inhibition of tumor metastasis by tetracycline compounds.

Metastatic tumor foci (MTF) were visible in lungs fixed in Bouin's fixative. Most of the MTF were less than 1 mm in diameter in all the treatment groups. FIG. 3B shows the number of metastatic foci in the lungs (Mean±SEM). As illustrated in FIG. 3B, the control group showed 59.5±13.9 MTF/rat (Mean±SD) and only 39.7±17.2 or 43.6±18.8 MTF/rat in low dose and high dose doxycycline-treated group, respectively. High dose CMT-3 group (40 mg/kg) had the most significant reduction in MTF, 28.9±15.4 MTF/rat, a 51% reduction in MTF. Histological examination of the lung sections did not reveal any apparent abnormality in tumor foci among various treatment groups.

EXAMPLE 5

Effect of Pretreatment on Tumor Growth and Metastasis

In another series of experiments, we examined whether predosing host animals with the drugs would affect tumor growth and metastasis, as seen for some other tumor systems. Daily gavage of control or drugs began 7 days prior to tumor cell injections ($2 \times 10^5$ cells/animal) and continued for a total of 21 days. Using this schedule, we found a decrease in tumor incidence and tumor growth rate. Tumor growth rates were calculated from thrice-weekly measurement of tumor volume with linear regression analysis of log-transformed volume measurements. Tumor growth rates determined by this method were then tested by Tukey-Kramer multiple comparison test and were found to be significantly different from the control group.

Figure 4A:
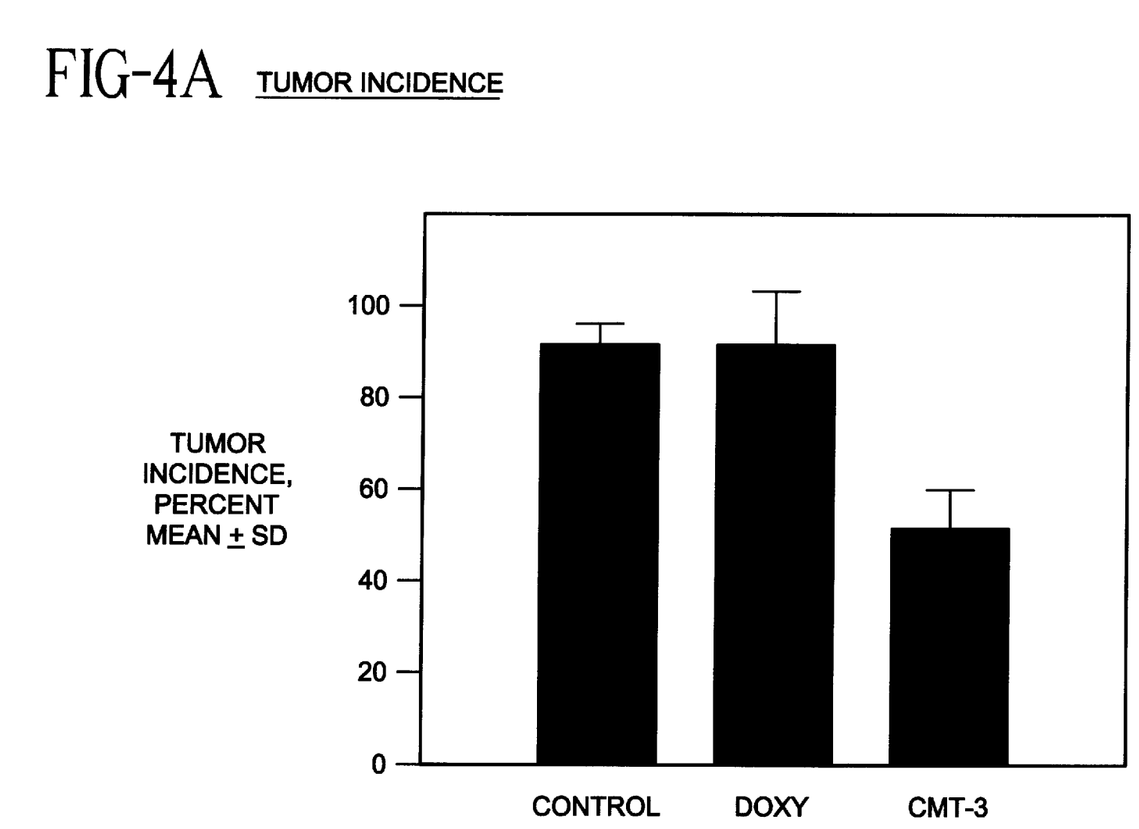
FIG. 4A is a histogram demonstrating the capacity of CMT-3 to reduce tumor incidence following implantation of tumor cells into test animals.

As shown in FIG. 4A, tumor incidence was>90% in control and doxycycline treated groups in three independent experiments. Surprisingly, however, tumor incidence in CMT-3-treated rats was significantly lower, 51±8.5% (p<0.01). Furthermore, a preparation of CMT-3 of greater purity reduced the tumor incidence to 43%. Thus, only CMT-3, and not the commercially available tetracycline, doxycycline, produced significant inhibition of the incidence of primary tumors. Applicants were especially surprised by the apparent remission of palpable tumors (i.e., reduction of tumor size) in rats treated with CMT-3. No comparable effect was observed for doxycycline. The rats with no primary tumor incidence remained tumor-free up to six months, at which time they were euthanized.

In addition, tumor growth rate in the CMT-3 -treated group was significantly lower, 20.2±3.5 days (CMT-3-treated) versus 15.9±2.0 days (control) to reach a tumor volume of 3 cm$^3$. It should be noted, however, the tumor growth rate was calculated from the subset of animals in which the tumors were measurable.

Figure 4B:
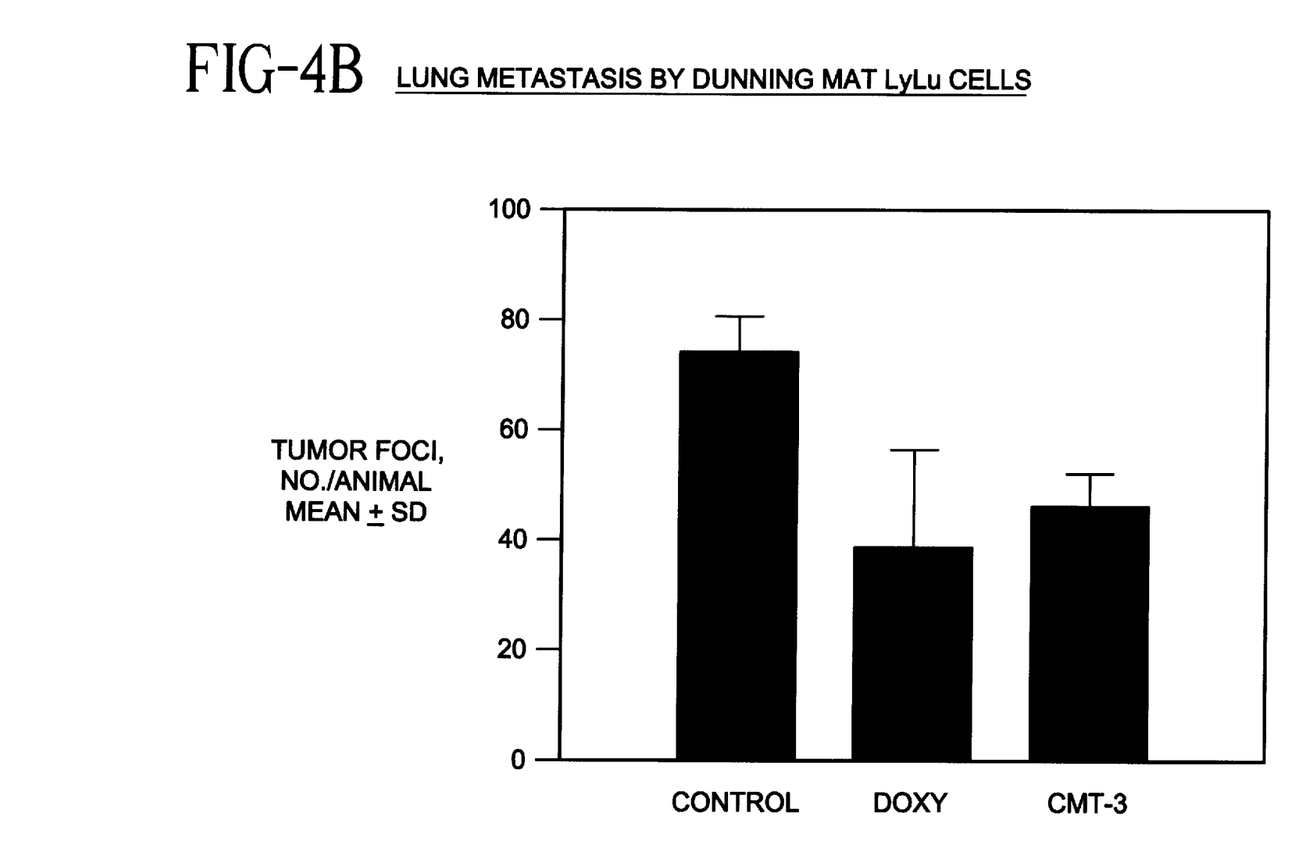
FIG. 4B is a histogram illustrating the inhibition of tumor metastasis by tetracycline compounds.

CMT-3 also inhibited tumor metastasis by predosing the animals with CMT-3. See FIG. 4B. This effect was comparable to that observed without predosing. The MTF in treated animals was 46.3±6.7 in the CMT-3-treated group versus 74.2±6.4 in controls, a 37.5% decrease. Data presented are Mean±SD from all the animals in which tumors grew to a size of≧10 cm$^3$.

None of the typical adverse effects of drug treatments, such as irritability, hypersensitivity to light, hair loss, or diarrhea were observed in association with the tetracycline treatments described hereinabove. As a gross measure of injury to normal tissue plausibly caused by doxycycline or CMT-3, animals were weighed before, during and after treatment, and all changes were examined. In all experiments, none of the animals showed a significant weight loss; instead, animals gained 8% to 12% weight during the course of the experiments.

Thus, while there have been described what are presently believed to be the preferred embodiments of the present invention, those skilled in the art will realize that other and further embodiments can be made without departing from the spirit of the invention, and it is intended to include all such further modifications and changes as come within the true scope of the claims set forth herein.

BIBLIOGRAPHY

The following publications, mentioned in the foregoing specification, are incorporated herein by reference for all that they disclose:

Zucker, S, R M Lysick, N S Ramamurthy, L M Golub, J M Wieman, and D P Wilkie, "Diversity of plasma membrane proteinases in mouse melanoma cells: Inhibition of collagenolytic activity and cytolytic activity by minocycline," *J Natl. Cancer Inst*. 75:517–525 (1985).

Golub, L M, N S Ramamurthy, and T F McNamara, *Crit. Rev. Oral Biol Med*. 2:297–322 (1991).

Golub, L M, T Sorsa, and K Suomalainen, *Curr. Opin. Dent*. 2:80–90 (1992).

DeClerck, Y A, H Shimada, S M Taylor, and K E Langley, *Annals N.Y. Acad. Sci*. 732:222–232 (1994).

Maragoudakis, M E, P Peristeris, E Missirlis, A Aletras, P Andriopoulou, and G Haralabopoulos, *Annals N.Y. Acad. Sci*. 732:280–293 (1994).

Mitscher, L. A., *The Chemistry of the Tetracycline Antibiotics*, Ch. 6, Marcel Dekker, New York (1978).

Uitto, V J, J D Firth, L Nip, and L M Golub, *Annals N.Y. Acad. Sci*. 732:140–151 (1994).

What is claimed is:

1. The method of inhibiting cancer growth in a mammal having a cancer, comprising administering to said mammal a cancer-inhibitory amount of 6-demethyl-6-deoxy-4-dedimethylaminotetracycline (CMT-3), wherein said cancer is selected from the group consisting of prostrate, breast, colon, lung and lymph cancers.

2. The method according to claim 1, wherein said cancer is a carcinoma.

3. The method according to claim 2, wherein said cancer is an adenocarcinoma.

4. The method according to claim 1, wherein said method comprises inhibiting cellular proliferation of said cancer.

5. The method according to claim 1, wherein said method comprises inhibiting invasiveness of said cancer.

6. The method according to claim 1, wherein said method comprises inhibiting metastasis of said cancer.

7. The method according to claim 1, wherein said tetracycline compound is administered in an amount sufficient to specifically inhibit expression of at least one matrix metalloproteinase by cells of said cancer.

8. The method according to claim 7, wherein said at least one matrix metalloproteinase comprises a gelatinase.

9. The method according to claim 8, wherein said at least one matrix metalloproteinase comprises gelatinase A or gelatinase B.

10. The method according to claim 1, further comprising treating said mammal with an adjunct antineoplastic modality.

11. The method according to claim 10, wherein said adjunct antineoplastic modality comprises chemotherapy, surgery, or radiotherapy.

12. The method of inhibiting cancer growth in a mammal having a cancer, comprising topically administering to said mammal a cancer-inhibitory amount of tetracyclinonitrile (CMT-2) wherein said cancer is selected from the group consisting of prostate, breast, colon, lung and lymph cancers.

13. A method of inhibiting cancer growth in a mammal having a prostate cancer, comprising administering to said mammal a cancer-inhibitory amount of 6-demethyl-6-deoxy-4-dedimethylaminotetracycline (CMT-3).

* * * * *

UNITED STATES PATENT AND TRADEMARK OFFICE
CERTIFICATE OF CORRECTION

PATENT NO. : 5,837,696
DATED : July 30, 1999
INVENTOR(S) : Golub et al.

It is certified that error appears in the above-indentified patent and that said Letters Patent is hereby corrected as shown below:

At Column 14, line 17, the patent now reads "The method"; this should read --A method--.

At Column 14, line 48, the patent now reads "The method"; this should read --A method--.

Signed and Sealed this

Third Day of April, 2001

*Attest:*

NICHOLAS P. GODICI

*Attesting Officer*  *Acting Director of the United States Patent and Trademark Office*